United States Patent [19]

Matsumoto

[11] Patent Number: 5,233,372
[45] Date of Patent: Aug. 3, 1993

[54] ILLUMINATING OPTICAL DEVICE

[75] Inventor: Kazuhiro Matsumoto, Kawasaki, Japan

[73] Assignee: Canon Kabushiki Kaisha, Tokyo, Japan

[21] Appl. No.: 772,955

[22] Filed: Oct. 8, 1991

[30] Foreign Application Priority Data

Oct. 16, 1990 [JP] Japan .................. 2-276763

[51] Int. Cl.⁵ ............................. A61B 3/10
[52] U.S. Cl. ................... 351/221; 351/206; 351/214
[58] Field of Search ............ 351/205, 206, 214, 221; 359/848, 641, 387; 362/216, 298, 302, 304; 354/62

[56]   References Cited
   U.S. PATENT DOCUMENTS

| | | |
|---|---|---|
| 4,747,030 | 5/1988 | Offner et al. .................. 362/302 |
| 4,820,037 | 4/1989 | Kohayakawa et al. . |
| 4,848,896 | 7/1989 | Matsumoto . |
| 4,952,049 | 8/1990 | Matsumoto . |
| 5,009,498 | 4/1991 | Gersten et al. .................. 351/206 |

FOREIGN PATENT DOCUMENTS 53-43277 4/1978 Japan .

Primary Examiner—Rodney B. Bovernick
Assistant Examiner—Hung Xuan Dang
Attorney, Agent, or Firm—Fitzpatrick, Cella, Harper & Scinto

[57]   ABSTRACT

An illuminating optical device includes a light source including two light emitting points which are symmetric with respect to an optical axis of the illuminating optical device, a first concave reflection mirror plane arranged behind the light source and symmetrically to the optical axis in order to form an image of the light source at a predetermined position of an illuminated area, and a second concave reflection mirror plane arranged more closely to the illuminated area than the first concave reflection plane and symmetrically to the optical axis in order to direct the light beam to the light emitting points of the light source.

18 Claims, 5 Drawing Sheets

1

ILLUMINATING OPTICAL DEVICE

BACKGROUND OF THE INVENTION

1. Field of the Invention

The present invention relates to an illuminating optical device used for photographing an eye fundus.

2. Related Background Art

A prior art illuminating optical device is built in an eye photographing apparatus, for example, and utilized to illuminate an eye fundus. When the eye fundus is photographed, light reflected by the eye fundus is directed to an imaging plane. Since the reflective index of a cornea is usually larger than that of the eye fundus, the eye to be checked is illuminated in a ring shape as shown in Japanese Patent Publication No. 53-43277 in order to suppress the reflection by the cornea and a light beam reflected by the eye fundus is taken out of a center area which is separate from the ring-shaped illumination area. This is the so-called ring shape illumination method. A stroboscope light source such as, a discharge tube is used to instantly irradiate with a strong illumination light the eye fundus.

However, in the prior art, only one or two, at most, forward light beams of the light beams emitted in every direction from the light emitting device such as the stroboscope light source are utilized and the light beams emitted in other directions do not contribute to the illumination of the eye fundus. As a result, in photographing the eye fundus, the photographed image may be not clear because of insufficient light. However, because the power supplied to the stroboscope light source is limited, an illumination light of a larger intensity is demanded.

SUMMARY OF THE INVENTION

It is an object of the present invention to provide an illuminating optical device which solves the problems of the prior art and efficiently utilizes a light beam emitted from a light source.

DETAILED DESCRIPTION OF THE PREFERRED EMBODIMENTS

Figure 1:
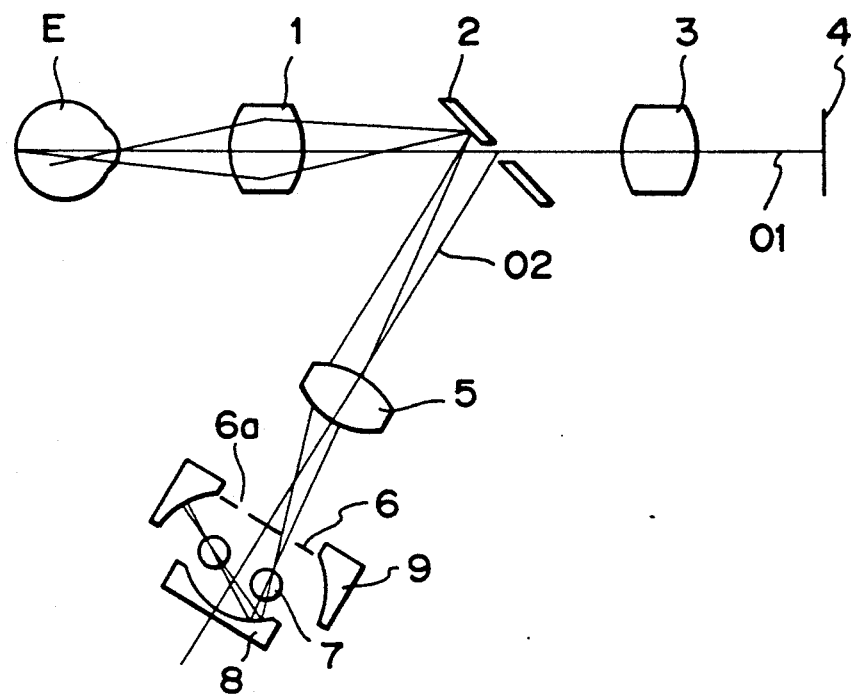
FIG. 1 shows a configuration of an embodiment of an illuminating optical device of the present invention.
Figure 2:
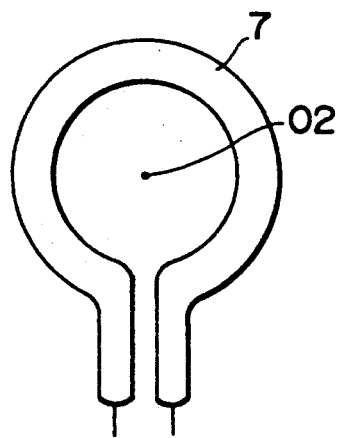
FIG. 2 shows a front view of a ring-shaped light source.
Figure 3:
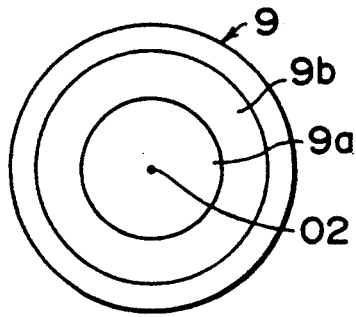
FIG. 3 shows a front view of a concave mirror.

FIG. 1 shows the configuration of one embodiment in which the present invention is applied to an eye fundus camera. An objective lens 1, an apertured mirror 2, a photographing lens 3 and a film 4 are sequentially arranged on an eye axis 01 of an eye E to be checked, and a relay lens 5 and an apertured iris 6 having a ring-shaped opening 6a are arranged on an optical axis 02 along the direction of reflection of the apertured mirror 2. A transparent stroboscope light source 7 having a ring shape of the same size as the opening 6a of the apertured iris 6, and a first concave mirror 8 which is larger than the stroboscope light source 7 and has a mirror plane facing the stroboscope light source 7 are arranged behind the apertured iris 6 as shown in a sectional view of FIG. 2 taken along a plane normal to the optical axis 02. A second concave mirror 9 having a light transmitting area 9a and a mirror plane 9b facing the stroboscope light source 7 is arranged on a side of the stroboscope light source 7 as shown in a front view of FIG. 3 which is viewed from the stroboscope light source 7. The mirror plane of the first concave mirror 8 is a spherical plane centered at the center of the ring (which is on the optical axis) of the stroboscope light source 7 and is constructed to focus the stroboscope light source 7 to the mirror plane as shown. The mirror plane of the second concave mirror 9 is a cylindrical mirror plane centered at the center of light emission of the stroboscope light source 7 in each sectional plane which contains the optical axis as shown in FIGS. 4A-4C, that is, a cylindrical mirror plane which reflects light beams emitted from the stroboscope light source 7 back to the emitting points.

In photographing, the stroboscope light source 7 emits a light beam, which travels along the optical axis 02, through the opening 6a of the apertured iris 6 and the relay lens 5, is reflected by the apertured mirror 2, through the objective lens 1 and reaches the eye E to illuminate the eye fundus from a periphery of the pupil. The light reflected by the eye fundus goes through the same path, through the aperture of the apertured mirror 2 and the photographing lens 3 and reaches the film 4 so that the eye fundus image is recorded on the film 4.

The effects of the first concave mirror 8 and the second concave mirror 9 are now explained. FIG. 4A shows an enlarged view of a section which contains the optical axis 02. In this plane, the light beams of the stroboscope light source 7 are emitted to all directions in the plane. If the first and second concave mirrors 8 and 9 are not properly arranged, only the light beam emitted in the direction A passes through the opening 6a of the apertured iris 6 as shown in FIG. 4B and other light beams are not utilized to illuminate the object.

Figure 4A:
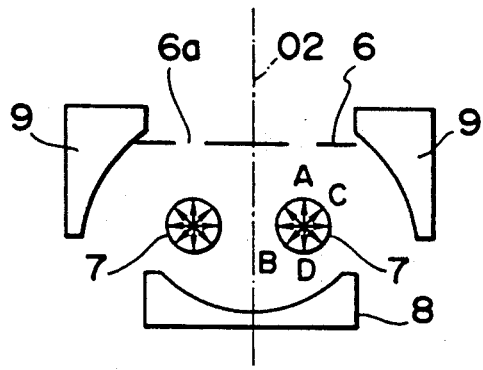
FIGS. 4A to 4E illustrate the direction of reflection of light beams.
Figure 4B:
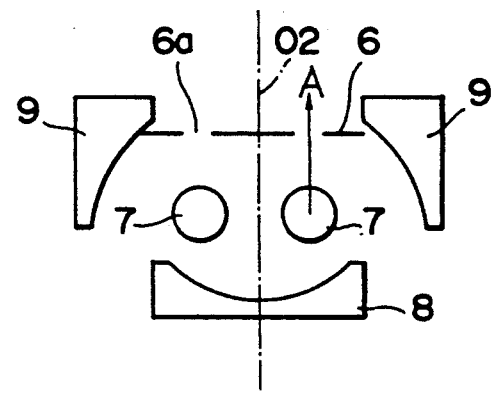
Figure 4C:
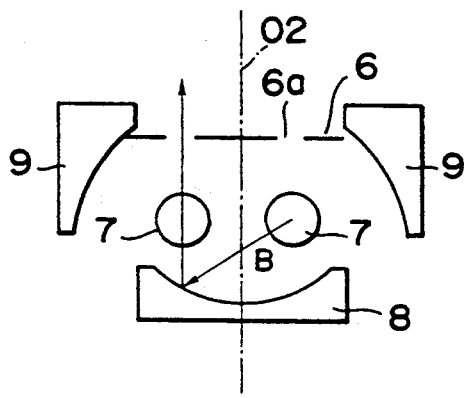
Figure 4D:
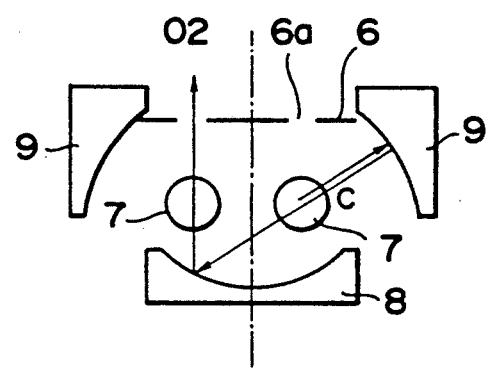
Figure 4E:
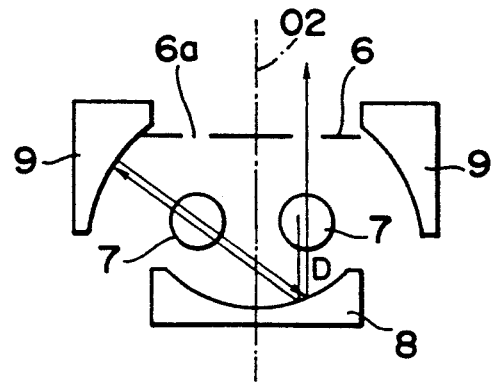

When the first concave mirror 8 and the second concave mirror 9 are arranged as they are in the present embodiment, the light beams emitted in the directions B, C and D shown in FIG. 4A travel as shown by arrows in FIGS. 4C, 4D and 4E, respectively, and reflected by the first concave mirror 8 and the second concave mirror 9 so that they pass through the opening 6a. The above explanation is for one sectional plane. Since the stroboscope light source 7 is of generally ring shape, the same is generally true for the light beams emitted by the stroboscope light, source 7. As a result, the intensity of light of the stroboscope light source 7 which reaches the eye fundus of the eye E is increased and a sharp image of the eye fundus is obtained.

Figure 5:
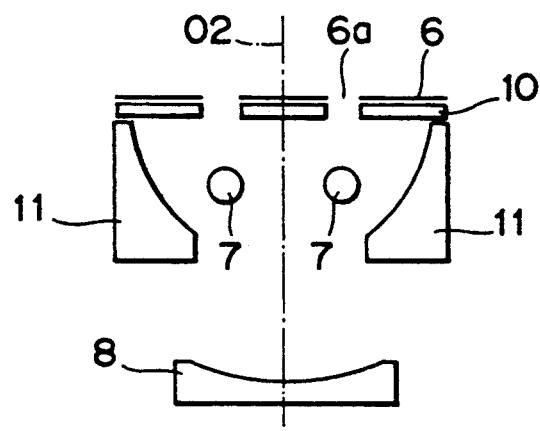
FIG. 5 shows the configuration of major portions of a second embodiment.

FIG. 5 shows a sectional view of a second embodiment which uses a combination of mirrors 10 and 11 instead of the mirror 9 of FIG. 4. The reflection mirror 10 having an opening which is of the same size and shape as that of the opening of the apertured iris 6 and has a mirror plane facing the stroboscope light source 7 is arranged behind the ring-shaped apertured iris 6, a first concave mirror 8 which is similar to that of the first embodiment is arranged behind the stroboscope light source 7, and the second concave mirror 11 which is of a ring shape and has a mirror plane facing the stroboscope light source 7 is arranged around the stroboscope light source 7. Other elements are same as those of the first embodiment. The second concave mirror 11 focuses a reflected image 7R of the stroboscope light source 7 by the reflection mirror 10 to a ring center 7R' of the stroboscope light source 7, for the light beam which is in the plane of the drawing, as shown by broken lines in FIG. 6A.

Figure 6A:
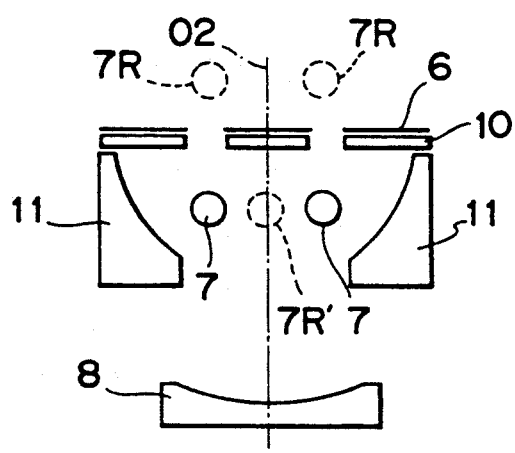
FIGS. 6A to 6C illustrate the direction of reflection of light beams.
Figure 6B:
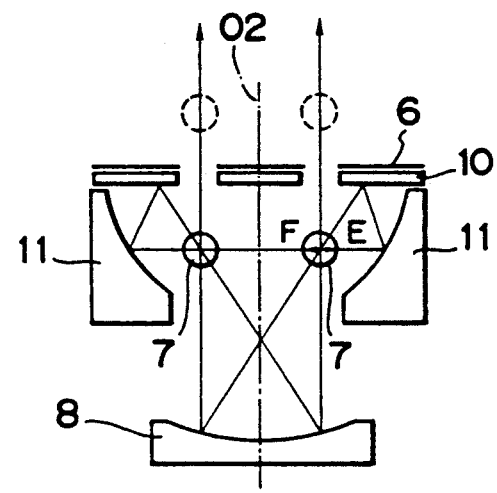
Figure 6C:
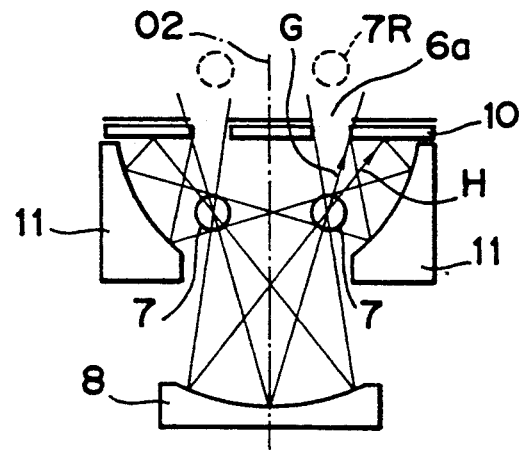

Accordingly, as shown by arrows in FIG. 6B, the light beams emitted from the stroboscope light source 7 to the directions E and F which are normal to the optical axis 02 are reflected by the second concave mirrors 11 as the light beams emitted from the ring center 7R' in the directions E and F are reflected, and they are directed to the point 7R, reflected by the reflection mirror 10 and return to the position of the stroboscope light source 7. They are further reflected by the first concave mirror 8 and pass through the opening of the apertured iris 6. As shown by arrows in FIG. 6C, the light beams emitted between the directions G and H are also reflected by the second concave mirror 11, reach the ring center 7R' shown in FIG. 6A, are successively reflected by the concave mirror 11, the reflection mirror 10 and the first concave mirror 8, and pass through the opening 6a of the apertured iris 6. Since the light beams emitted in the directions A to D shown in FIG. 4 are also utilized, it is more effective to increase the photographing light intensity.

Figure 7:
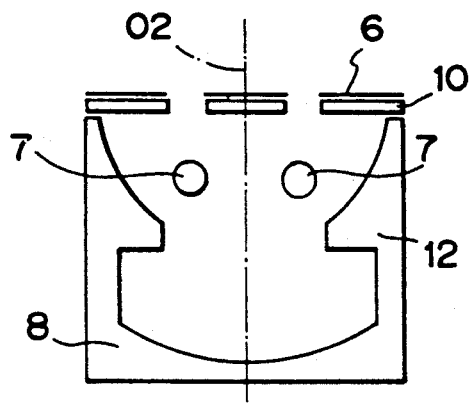
FIGS. 7, 8, 9 and 10 show configurations of other embodiments.

As shown in FIG. 7, instead of the first concave mirror 8 and the second concave mirror 11, a reflection mirror 12 having a combined mirror plane may be used.

Figure 11:
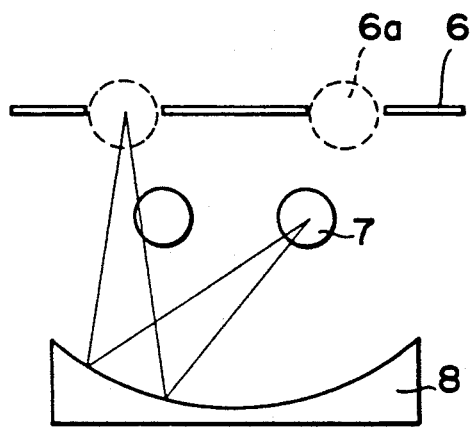
FIGS. 11, 12 and 13 show modifications of the present invention.

In the above embodiment, the first concave mirror 8 has the mirror plane which is shaped to focus the ring-shaped light source 7 to the concave mirror 8. However, as shown in FIG. 11, the light of the light source can be more efficiently utilized for the illumination when the ring-shaped light source 7 is focused to the opening 6a of the apertured iris 6.

Figure 12:
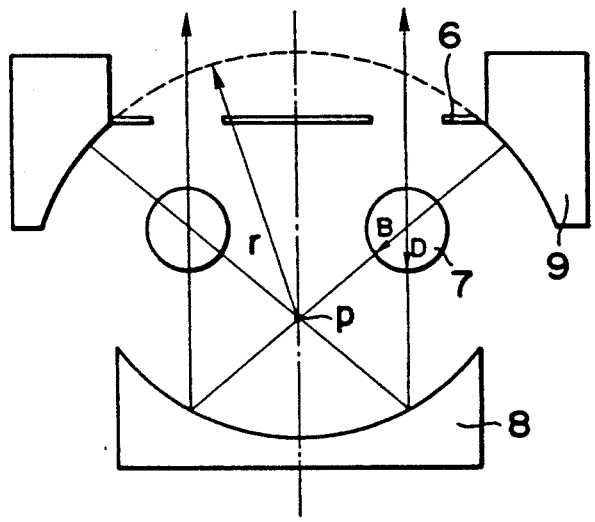

As shown in FIG. 12, the second concave mirror 9 may have a spherical plane (radius of curvature r in FIG. 12) centered in a vicinity of a point P at which the light beam emitted to the direction B or D in FIG. 4A crosses the optical axis.

Figure 13:
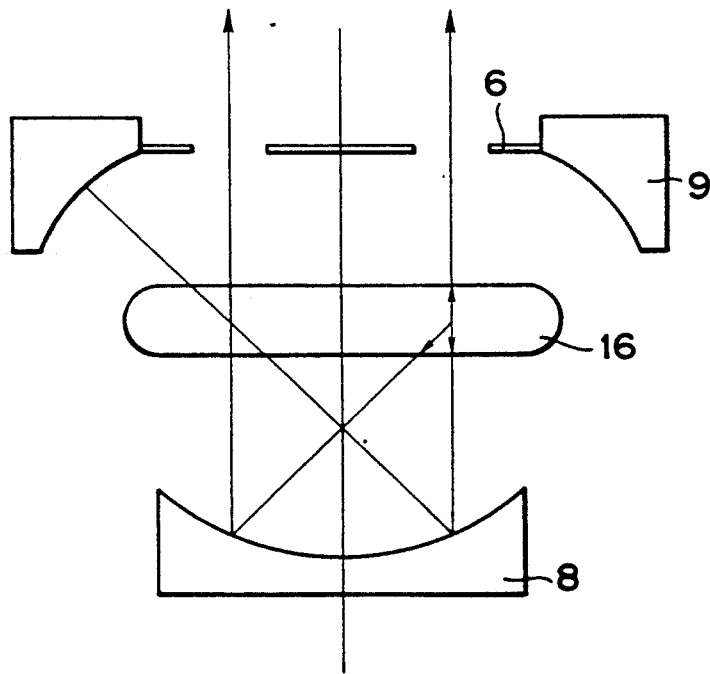

In the present embodiment, the stroboscope light source 7 is of a ring shape. However, as shown in FIG. 13, a linear tube type stroboscope light source 16 may be used instead of the ring-shaped stroboscope light source.

Figure 8:
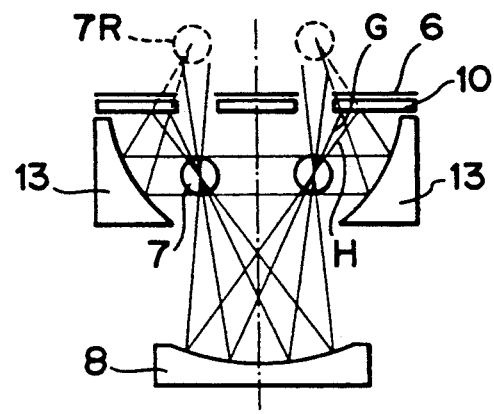

FIG. 8 shows a modification of the embodiment of FIG. 6. In the embodiment of FIG. 6, when the optical system is cut along a sectional plane which contains the optical axis and the light beams in the sectional plane are considered, the second reflection mirror 11 is constructed to focus the reflected image 7R of the light source 7 by the reflection mirror 10 on the optical axis as shown by 7R' in FIG. 6A. In the embodiment of FIG. 8, the shape and the position of the second reflection mirror 13 are selected such that the light beam emitted from the light source 7 and reflected by the reflection mirror 10 is collimated and passes through two areas of the light source 7 (which are symmetrical about the optical axis).

Figure 9:
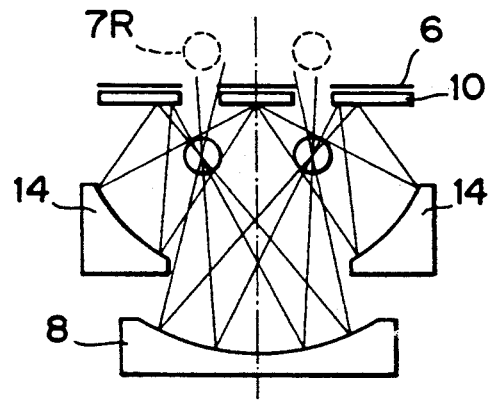

In an embodiment shown in FIG. 9, the shape and the position of the second reflection mirror 14 are selected such that the light beam emitted from the light source 7 and reflected by the reflection mirror 10 passes through the light source 7 and is focused to a cross-point of the optical axis and the reflection mirror 10.

Figure 10:
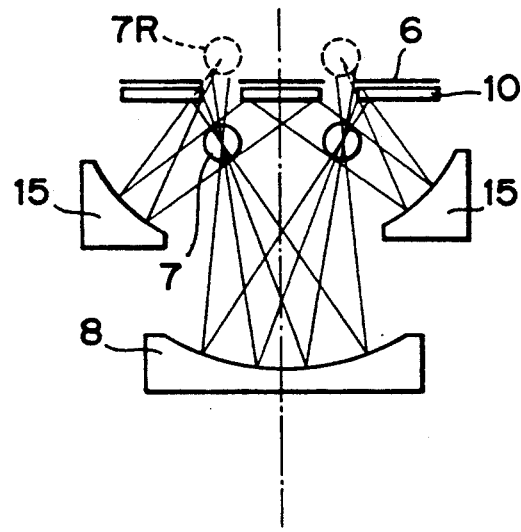

In a modification shown in FIG. 10, the shape and the position of the second reflection mirror 15 are selected such that the light beam emitted from the light source 7 and reflected by the reflection mirrors 10 and 15 is collimated, passes through the light source 7 and is reflected by a third reflection mirror in a vicinity of the optical axis.

In each of the above embodiments, the light beam emitted by the light source forms a light path which is symmetric about the optical axis, and the light path passes through the light source a plurality of times. Accordingly, the light beams emitted from the light source in a plurality of directions are efficiently directed in one direction and the object can be efficiently illuminated.

What is claimed is:

1. An illuminating optical device for illuminating an object, comprising:

a light source including at least two light emitting points symmetric with respect to an optical axis of the illuminating optical device, for emitting light beams approximately toward the object from the two light emitting points without any reflections from said device;

a first concave reflection mirror surface arranged behind said light source and symmetrically with respect to the optical axis to form an image of said light source at a predetermined position directed to an illuminated area, said first concave reflection mirror surface being arranged to reflect a first part of the light beams emitted directly from the two light emitting points approximately toward the object directly; and a second concave reflection mirror surface arranged closer to the object along the optical axis than said first concave reflection mirror surface and symmetrically with respect to the optical axis to direct the light beam to the light emitting points of said light source, said second concave reflection mirror surface being arranged to reflect light beams each travelling from one of the two light emitting points to said first concave reflection mirror surface so that the each of the light beams is directed approximately toward the object by said first concave reflection mirror surface;

a second part of the light beams travelling directly from the light emitting points of said light source to said first concave reflection mirror surface and being directed to said second concave reflection mirror surface by said first concave reflection mirror surface so that the second part of the light beams are reflected by said second and first concave reflection mirror surfaces in sequence and then directed approximately toward the object.

2. An illuminating optical device according to claim 1 further comprising a third mirror surface arranged closer to the object along the optical axis than said second concave reflection mirror surface and symmetrically with respect to the optical axis to direct the light beam to the light emitting points of said light source in cooperation with said second concave reflection mirror surface.

3. An illuminating optical device according to claim 2 wherein said first concave reflection mirror surface directs the light beam emitted from one of the light emitting points of said light source to the other light emitting point.

4. An illuminating optical device according to claim 3 wherein said first concave reflection mirror surface images one of the light emitting points of said light source to the other light emitting point.

5. An illuminating optical device according to claim 2 wherein aid light source is of a ring shape.

6. An illuminating optical device according to claim 5 further comprising a ring-shaped apertured iris arranged to face said light source on the side of said light source facing the illuminated area.

7. An illuminating optical device according to claim 6 wherein said first concave reflection mirror surface images the light emitting points of said light source to said ring-shaped apertured iris.

8. An illuminating optical device according to claim 6 wherein said third mirror is provided with said ring-shaped aperture iris and arranged close to said light source.

9. An illuminating optical device according to claim 1 wherein said first concave reflection mirror surface directs the light beam emitted from one of the light emitting points of said light source to the other light emitting point.

10. An illuminating optical device according to claim 9 wherein said first concave reflection mirror surface images one of the light emitting points of said light source to the other light emitting point.

11. An illuminating optical device according to claim 1 wherein said light source is of a ring shape.

12. An illuminating optical device according to claim 11 further comprising a ring-shaped apertured iris arranged to face said light source on the side of said light source facing the illuminated area.

13. An illuminating optical device according to claim 12 wherein said first concave reflection mirror surface images the light emitting points of said light source to said ring-shaped apertured iris.

14. An illuminating device for an eye, comprising:
a light source including at least two light emitting points symmetric with respect to an optical axis of the illuminating device, for emitting light beams approximately toward the eye from the two light emitting points without any reflection from said device;
a first concave reflection mirror surface arranged behind said light source and symmetrically with respect tot he optical axis to form an image of said light source at a predetermined position directed to the eye, said first concave reflection mirror surface being arranged to reflect a first part of light beams emitted directly from the two light emitting points approximately toward the eye directly; and
a second concave reflection mirror surface arranged closer to the eye along the optical axis than said first concave reflection mirror surface and symmetrically with respect to the optical axis to direct the light beam to the light emitting points of said light source, said second concave reflection mirror plane being arranged to reflect light beams each travelling from one of the two light emitting points to said first concave reflection mirror surface so that the each of the light beams is directed approximately toward the eye by said first concave reflection mirror surface;
a second part of the light beams travelling directly from the light emitting points of said light source to said first concave reflection mirror surface and being directed to the second concave reflection mirror surface by said first concave reflection mirror surface so that the second part of the light beams are reflected by said second and first concave reflection mirror surfaces in sequence and then directed approximately toward the eye.

15. An eye fundus camera comprising:
photographing means for photographing an eye fundus;
illuminating means for illuminating the eye fundus;
said illumination means including:
a light source including at least two light emitting points symmetric with respect to an optical axis of the illuminating device, for emitting light beams approximately toward the eye fundus from the two light emitting points without any reflections from said device;
a first concave reflection mirror surface arranged behind said light source and symmetrically with respect to the optical axis to form an image of said light source at a predetermined position directed to the eye fundus, said first concave reflection mirror surface being arranged to reflect a first part of the light beams emitted directly from the two light emitting points approximately toward the eye fundus directly; and
a second concave reflection mirror surface arranged closer to the eye fundus along the optical axis than said first concave reflection mirror surface and symmetrically with respect to the optical axis to direct the light beam to the light emitting points of said light source, said second concave reflection mirror plane being arranged to reflect light beams each travelling from one of the two light emitting points to said first concave reflection mirror surface so that the each of the light beams is directed approximately toward the eye fundus by said first concave reflection mirror surface;
a second part of the light beams travelling directly from the light emitting points of said light source to said first concave reflection mirror surface being directed to the second concave reflection mirror surface by said first concave reflection mirror surface so that the second part of the light beams are reflected by said second and first concave reflection mirror surfaces in sequence and then directed approximately toward the eye fundus.

16. An illuminating optical device for illuminating an object, comprising:
a light source including at least two light emitting points symmetric with respect to an optical axis of the illuminating optical device, for emitting light beams approximately toward the object from the two light emitting points without any reflections from said device;
a first concave reflection mirror surface arranged behind said light source and symmetrically with respect to the optical axis to form an image of said light source at a predetermined position directed to an illuminated area, said first concave reflection mirror surface being arranged to reflect at least a part of light beams emitted directly from the two light emitting points approximately toward the object directly; and
a second concave reflection mirror surface arranged closer to the eye along the optical axis than said first concave reflection mirror surface and symmetrically with respect to the optical axis to direct the light beam to the light emitting points of said light source, said second concave reflection mirror plane being arranged to reflect light beams each travelling from one of the two light emitting points to said first concave reflection mirror surface so that the each of the light beams is directed approximately toward the object by said first concave reflection mirror surface.

17. An illuminating device for an eye, comprising:
a light source including at least two light emitting points symmetric with respect to an optical axis of the illuminating device, for emitting light beams approximately toward the eye from the two light emitting points without any reflections from said device;
a first concave reflection mirror surface arranged behind said light source and symmetrically with respect o the optical axis to form an image of said light source at a predetermined position directed to the eye, said first concave reflection mirror surface being arranged to reflect at least a part of the light beams emitted directly from the two light emitting points approximately toward the eye directly; and
a second concave reflection mirror surface arranged closer to the eye along the optical axis than said first concave reflection mirror surface and symmetrically with respect to the optical axis to direct the light beam to the light emitting points of said light source, and second concave reflection mirror plane being arranged to reflect light beams each travelling from one of the two emitting points to said first concave reflection mirror surface so that the each of the light beams is directed approximately toward the eye by said first concave reflection mirror surface.

18. An eye fundus camera comprising:
photographing means for photographing an eye fundus;
illumination means for illuminating the eye fundus;
said illumination means including:
a light source including at least two light emitting points symmetric with respect to an optical axis of the illuminating device, for emitting light beams approximately toward the eye fundus from the two light emitting points without any reflections from said device;
a first concave reflection mirror surface arranged behind said light source and symmetrically with respect tot he optical axis to form an image of said light source at a predetermined position directed to the eye fundus, said first concave reflection mirror surface being arranged to reflect at least a part of the light beams emitted directly from the two light emitting points approximately toward the eye fundus direction directly; and
a second concave reflection mirror surface arranged closer to the eye fundus along the optical axis than said first concave reflection mirror surface and symmetrically with respect to the optical axis to direct the light beam tot he light emitting points of said light source, said second concave reflection mirror plane being arranged to reflect light beams each travelling from one of the two light emitting points to said first concave reflection mirror surface so that the each of the light beams is directed approximately toward the eye fundus by said first concave reflection mirror surface.

* * * * *

UNITED STATES PATENT AND TRADEMARK OFFICE
CERTIFICATE OF CORRECTION

PATENT NO. : 5,233,372
DATED : August 3, 1993
INVENTOR(S) : KAZUHIRO MATSUMOTO

It is certified that error appears in the above-indentified patent and that said Letters Patent is hereby corrected as shown below:

COLUMN 1
    Line 21, "as," should read --as--.

COLUMN 2
    Line 22, "4A-4C," should read --4A-4E,--.

COLUMN 3
    Line 13, "to" (first occurrence) should read --in--.
    Line 44, "to" should read --in--.

COLUMN 5
    Line 8, "aid" should read --said--.
    Line 19, "aperture" should read --apertured--.
    Line 49, "tot he" should read --to the--.

UNITED STATES PATENT AND TRADEMARK OFFICE
CERTIFICATE OF CORRECTION

PATENT NO. : 5,233,372
DATED : August 3, 1993
INVENTOR(S) : KAZUHIRO MATSUMOTO

It is certified that error appears in the above-indentified patent and that said Letters Patent is hereby corrected as shown below:

COLUMN 7
   Line 19, "o" should read --to--.

COLUMN 8
   Line 16, "tot he" should read --to the--.
   Line 28, "tot he" should read --to the--.

Signed and Sealed this

Twenty-first Day of June, 1994

Attest:

BRUCE LEHMAN

Attesting Officer     Commissioner of Patents and Trademarks